United States Patent
Hazen et al.

(10) Patent No.: US 12,055,535 B2
(45) Date of Patent: *Aug. 6, 2024

(54) TRIMETHYLAMINE COMPOUNDS AS RISK PREDICTORS OF CARDIOVASCULAR DISEASE

(71) Applicant: The Cleveland Clinic Foundation, Cleveland, OH (US)

(72) Inventors: Stanley L. Hazen, Pepper Pike, OH (US); Zeneng Wang, Cleveland, OH (US); Bruce S. Levison, Twinsburg, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1058 days.

This patent is subject to a terminal disclaimer.

(21) Appl. No.: 16/781,409

(22) Filed: Feb. 4, 2020

(65) Prior Publication Data

US 2020/0173979 A1    Jun. 4, 2020

Related U.S. Application Data

(60) Continuation of application No. 15/234,050, filed on Aug. 11, 2016, now Pat. No. 10,551,372, which is a division of application No. 12/746,262, filed as application No. PCT/US2008/085648 on Dec. 5, 2008, now Pat. No. 9,423,405.

(60) Provisional application No. 61/102,896, filed on Oct. 6, 2008, provisional application No. 60/992,396, filed on Dec. 5, 2007.

(51) Int. Cl.
| | |
|---|---|
| *G01N 33/48* | (2006.01) |
| *G01N 33/483* | (2006.01) |
| *G01N 33/49* | (2006.01) |
| *G01N 33/493* | (2006.01) |
| *G01N 33/68* | (2006.01) |
| *G01N 33/92* | (2006.01) |
| *H01J 49/00* | (2006.01) |

(52) U.S. Cl.
CPC ........... *G01N 33/49* (2013.01); *G01N 33/493* (2013.01); *G01N 33/6893* (2013.01); *G01N 33/92* (2013.01); *H01J 49/0036* (2013.01); *G01N 2800/32* (2013.01); *G01N 2800/323* (2013.01); *G01N 2800/50* (2013.01); *G01N 2800/52* (2013.01); *G01N 2800/56* (2013.01); *Y10T 436/174614* (2015.01)

(58) Field of Classification Search
None
See application file for complete search history.

(56) References Cited

U.S. PATENT DOCUMENTS

| | | | |
|---|---|---|---|
| 6,040,147 A | 3/2000 | Ridker et al. | |
| 6,680,302 B2 | 1/2004 | Seidman et al. | |
| 6,762,052 B1 | 7/2004 | Cashman et al. | |
| 9,423,405 B2* | 8/2016 | Hazen | G01N 33/493 |
| 10,551,372 B2* | 2/2020 | Hazen | G01N 33/493 |
| 2004/0005612 A1* | 1/2004 | Giudice | C12Q 1/6883 |
| | | | 435/6.11 |
| 2004/0058386 A1* | 3/2004 | Wishart | G01R 33/4625 |
| | | | 435/7.1 |
| 2004/0121305 A1 | 6/2004 | Wiegand et al. | |
| 2005/0016104 A1 | 5/2005 | Rosenberg | |
| 2006/0073213 A1 | 4/2006 | Hotamisligil et al. | |
| 2006/0099582 A1 | 5/2006 | Papadopoulos et al. | |
| 2006/0177435 A1 | 8/2006 | Tsimikas | |
| 2006/0233817 A1* | 10/2006 | Hansson | C07K 14/775 |
| | | | 530/359 |
| 2012/0157397 A1 | 6/2012 | Hazen et al. | |
| 2016/0343559 A1 | 11/2016 | Kinoshita et al. | |

FOREIGN PATENT DOCUMENTS

| | | |
|---|---|---|
| EP | 1731161 | 12/2006 |
| WO | WO 2007127192 | 11/2007 |
| WO | WO 200973839 | 6/2009 |

OTHER PUBLICATIONS

"Definition of Plasma," Merriam-Webster.com, Jan. 17, 2018 (Year: 2018).
"Definition of Serum," Merriam-Webster.com, Jan. 17, 2018 (Year: 2018).
Bain et al., Quantifying trimethylamine and trimethylamine-N-oxide in human plasma: interference from endogenous quaternary ammonium compounds. Anal Biochem. Nov. 15, 2004;334(2):403-5.
Fish, http://en.wikipedia.org/wiki/Fish, on Nov. 2, 2014, 11 pages.
Fu et al., Specific sequence motifs direct the oxygenation and chlorination of tryptophan by myeloperoxidase.Biochemistry. Mar. 28, 2006;45(12):3961-71.

(Continued)

*Primary Examiner* — Bradley L. Sisson
(74) *Attorney, Agent, or Firm* — Jason R. Bond; Casimir Jones, S.C.

(57) ABSTRACT

Methods of characterizing a test subject's risk of having or developing cardiovascular disease are provided. The methods include using an analytic device to determine levels of choline-related trimethylamine-containing compounds such as trimethylamine N-oxide, choline, or betaine in a biological sample obtained from the subject and comparing the levels of the choline-related trimethylamine-containing compound in the subject's biological sample to a control value. The test subject's risk of having cardiovascular disease is then characterized as higher if the levels of the choline-related trimethylamine-containing compound are higher than the control value. Also provided are methods of identifying a subject at risk of experiencing a complication of atherosclerotic cardiovascular disease, and methods of evaluating the efficacy of a cardiovascular therapeutic agent in a subject with cardiovascular disease using levels of choline-related trimethylamine-containing compounds.

10 Claims, 13 Drawing Sheets

(56) References Cited

OTHER PUBLICATIONS

Harrison's 15th Edition Principles of Internal Medicine, vols. 1-2, 2001, TOC only, 17 pages.
International Search Report and Written Opinion for PCT/US2008/085648, mailed Feb. 19, 2009, 7 pages.
Knapp et al., Clincial Epidermiology and Biostatistics. Harwal Publishing Company, Malvern, PA, 1992, TOC only, 8 pages.
Mammal, retrieved from http://en.wikipedia.org/wiki/Mammals, on Sep. 22, 2011, 17 pages.
Murinae, http://en.wikipedia.org/wiki/Murinae, on Mar. 18, 2013, 21 pages.
Supplementary European Search Report for EP Patent Application 08857658.9, dated Nov. 4, 2010, 6 pages.
Wang et al., Metabolomics studies implicate choline metabolism and gut flora in cardiovascular disease (CVD) pathogenesis. Abstract, 6th Annual Medical Innovation Summit, Cleveland, OH, Nov. 10-12, 2008, 1 page.

\* cited by examiner

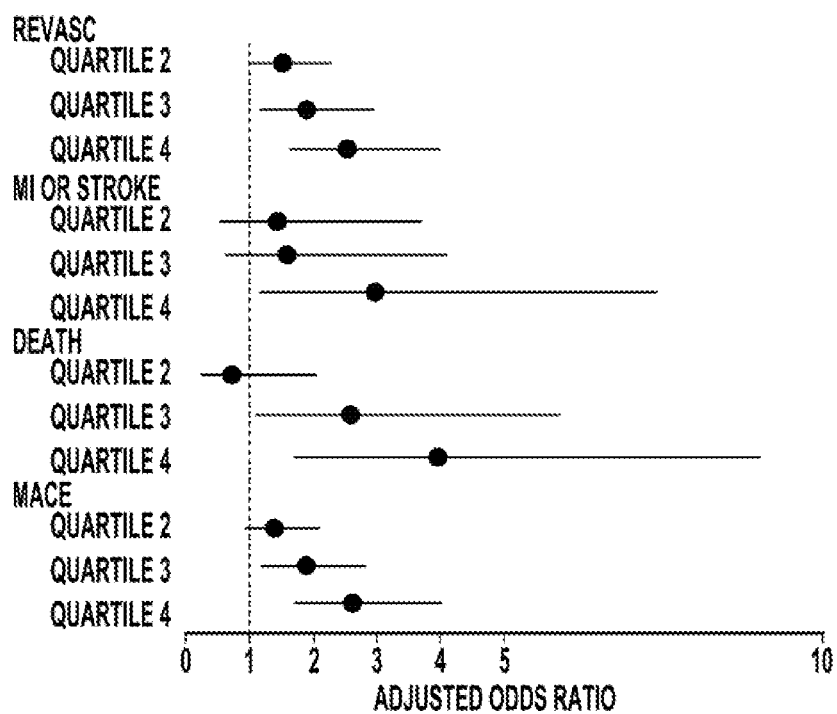

TRIMETHYLAMINE COMPOUNDS AS RISK PREDICTORS OF CARDIOVASCULAR DISEASE

CROSS-REFERENCE TO RELATED APPLICATIONS

This application is a continuation of U.S. patent application Ser. No. 15/234,050, filed Aug. 11, 2016, now allowed, which is a divisional of U.S. patent application Ser. No. 12/746,262, filed Jun. 4, 2010, now allowed, which is a § 371 national entry application of PCT/US2008/085648, filed Dec. 5, 2008, which claims the benefit of U.S. Provisional Application No. 61/102,896 filed Oct. 6, 2008 and U.S. Provisional Application No. 60/992,396 filed Dec. 5, 2007, each of which are incorporated by reference in their entireties.

STATEMENT REGARDING FEDERAL FUNDING

This invention was made with government support under HL076491 awarded by the National Institutes of Health. The government has certain rights in the invention.

FIELD OF THE INVENTION

The present invention relates to the field of cardiovascular disease. More specifically, it relates to markers and methods for determining whether a subject, particularly a human subject, is at risk of developing cardiovascular disease, having cardiovascular disease, or experiencing a complication of cardiovascular disease, e.g. an adverse cardiac event, within the ensuing year, two years, and/or three years. The present application also relates to the use of such markers and methods for monitoring the status of cardiovascular disease in a subject or the effects of therapeutic agents on subjects with cardiovascular disease.

BACKGROUND

Cardiovascular disease (CVD) is the general term for heart and blood vessel diseases, including atherosclerosis, coronary heart disease, cerebrovascular disease, aorto-iliac disease, and peripheral vascular disease. Subjects with CVD may develop a number of complications, including, but not limited to, myocardial infarction, stroke, angina pectoris, transient ischemic attacks, congestive heart failure, aortic aneurysm and death. CVD accounts for one in every two deaths in the United States and is the number one killer disease. Thus, prevention of cardiovascular disease is an area of major public health importance.

A low-fat diet and exercise are recommended to prevent CVD. In addition, a number of therapeutic agents may be prescribed by medical professionals to those individuals who are known to be at risk having CVD. These include lipid-lowering agents that reduce blood levels of cholesterol and triglycerides, agents that normalize blood pressure, agents, such as aspirin, or platelet ADP receptor antagonists that prevent activation of platelets and decrease vascular inflammation (e.g., clopidogrel and ticlopidine), and pleiotropic agents such as peroxisome proliferator activated receptor (PPAR) agonists, with broad-ranging metabolic effects that reduce inflammation, promote insulin sensitization, improve vascular function, and correct lipid abnormalities. More aggressive therapy, such as administration of multiple medications or surgical intervention may be used in those individuals who are at high risk of having CVD. Since CVD therapies may have adverse side effects, it is desirable to have methods for identifying those individuals, who are at risk, particularly those individuals who are at high risk of experiencing an adverse cardiac event near term.

Currently, several risk factors are used by medical professionals to assess an individual's risk of developing or having CVD and to identify individuals at high risk. Major risk factors for cardiovascular disease include age, hypertension, family history of premature CVD, smoking, high total cholesterol, low HDL cholesterol, obesity and diabetes. The major risk factors for CVD are additive, and are typically used together by physicians in a risk prediction algorithm to target those individuals who are most likely to benefit from treatment for CVD. These algorithms achieve a high sensitivity and specificity for predicting risk of CVD within 10 years. However, the ability of the present algorithms to predict a higher probability of developing CVD is limited. Among those individuals with none of the current risk factors, the 10-year risk for developing CVD is still about 2%. In addition, a large number of CVD complications occur in individuals with apparently low to moderate risk profiles, as determined using currently known risk factors. Thus, there is a need to expand the present cardiovascular risk algorithm to identify a larger spectrum of individuals at risk for or affected with CVD.

The mechanism of atherosclerosis is not well understood. Over the past decade a wealth of clinical, pathological, biochemical and genetic data support the notion that atherosclerosis is a chronic inflammatory disorder. Acute phase reactants (e.g. C-reactive protein, complement proteins), sensitive but non-specific markers of inflammation, are enriched in fatty streaks and later stages of atherosclerotic lesions. In a recent prospective clinical trial, base-line plasma levels of C-reactive protein independently predicted risk of first-time myocardial infarction and stroke in apparently healthy individuals. U.S. Pat. No. 6,040,147 describes methods which use C-reactive protein, cytokines, and cellular adhesion molecules to characterize an individual's risk of developing a cardiovascular disorder. Although useful, these markers may be found in the blood of individuals with inflammation due to causes other than CVD, and thus, these markers may not be specific enough. Moreover, modulation of their levels has not been shown to predict a decrease in the morbidity or mortality of CVD. Accordingly, there exists a need for additional markers for assessing a subject's risk of CVD.

SUMMARY OF THE INVENTION

One aspect of the present invention provides a method of identifying a subject at risk of experiencing a complication of atherosclerotic cardiovascular disease within the ensuing three years. The method includes (a) determining levels of a choline-related trimethylamine (TMA)-containing compound using an analytic device in a biological sample obtained from the subject, and (b) comparing levels of the choline-related trimethylamine-containing compound in the biological sample to a control value; wherein a test subject whose levels of the trimethylamine-containing compound in the biological sample are elevated as compared to the control value is at risk of experiencing a complication of atherosclerotic disease within the ensuing three years. In some embodiments, the method further comprises the step of characterizing the test subject's risk of experiencing a complication with the ensuing three years as higher if levels of the choline related trimethylamine-containing compound are higher than the control value and lower if levels of the choline-related trimethylamine-containing compound are lower than the control value. In some embodiments the method further comprises the step of displaying the results of step (b). In one embodiment of the present methods, the complications one or more of the following: non-fatal myocardial infarction, stroke, angina pectoris, transient ischemic attacks, congestive heart failure, aortic aneurysm, and death. In another embodiment the complication is major adverse cardiac event (MACE; one or more of the following conditions: non-fatal MI, stroke, need for revascularization (revascularization) or death).

Another aspect of the present invention provides a method of characterizing a subject's risk of having cardiovascular disease, including atherosclerotic cardiovascular disease. The method includes (a) determining levels of a choline-related trimethylamine-containing compound using an analytic device in a biological sample obtained from the subject, and (b) comparing levels of a choline-related trimethylamine-containing compound in the biological sample to a control value; wherein a test subject whose levels of the trimethylamine-containing compound in the biological sample are elevated as compared to the control value is characterized as being at risk of having cardiovascular disease. In some embodiments, the method further comprises the step of characterizing the subject's risk of having cardiovascular disease as higher if levels of the choline-related trimethylamine-containing compound are higher than the control value, and lower if levels of the choline-related trimethylamine-containing compound are lower than the control value. In some embodiments the method further comprises the step of displaying the results of step (b).

Another aspect of the present invention provides a method of characterizing a subject's risk of developing cardiovascular disease, including atherosclerotic cardiovascular disease. The method includes (a) determining levels of a choline-related trimethylamine-containing compound using an analytic device in a biological sample obtained from the subject, and (b) comparing levels of a choline-related trimethylamine-containing compound in the biological sample to a control value; wherein a test subject whose levels of the trimethylamine-containing compound in the biological sample are elevated as compared to the control value is characterized as being at risk of developing cardiovascular disease. In some embodiments, the method further comprises the step of characterizing the subject's risk of developing cardiovascular disease as higher if levels of the choline-related trimethylamine-containing compound are higher than the control value, and lower if levels of the choline-related trimethylamine-containing compound are lower than the control value. In some embodiments the method further comprises the step of displaying the results of step (b).

Another aspect of the present invention provides a method of evaluating the efficacy of a CVD therapeutic agent in a subject with cardiovascular disease, including atherosclerotic cardiovascular disease. The method includes determining levels of a choline-related trimethylamine-containing compound using an analytic device in a biological sample obtained from the subject during or after administration of the therapeutic agent, comparing levels of the choline-related trimethylamine-containing compound in the biological sample to a predetermined value, and determining the CVD therapeutic agent to be efficacious if levels of the choline-related trimethylamine-containing compound are lower than the predetermined value. In one embodiment of the method, the predetermined value is based on levels of a choline-related trimethylamine-containing compound in a comparable biological sample taken from the subject prior to administration of the CVD therapeutic agent. In a further embodiment, the predetermined value is based on levels of a choline-related trimethylamine-containing compound in a comparable biological sample taken from control subjects that do not have any signs or symptoms of cardiovascular disease.

In one embodiment of the present methods, the choline-related trimethylamine-containing compound is trimethylamine-N-oxide, choline, or betaine. In an additional embodiment, the compound is trimethylamine-N-oxide. In a further embodiment, the compound is choline or betaine. In another embodiment, the compound is a plurality of choline-related trimethylamine-containing compounds In one embodiment of the present methods, the biological sample is whole blood, serum, plasma, urine, cerebrospinal fluid, or bronchoalveolar lavage. In a further embodiment, the biological sample is blood serum or plasma.

In one embodiment of the present methods, the subject is a smoker, whereas in other embodiments the subject is a non-smoker. In some embodiments of the present methods, the subject does not have any signs or symptoms of cardiovascular disease.

In one embodiment of the present methods, the analytic device is a mass spectrometer.

BRIEF DESCRIPTION OF THE FIGURES

FIG. 4A shows plasma TMANO in subjects with (n=632) and without (n=361) atherosclerotic CVD. FIG. 4B shows the frequency of atherosclerotic CVD, coronary artery disease (CAD) and peripheral artery disease (PAD) according to quartiles of TMANO. P values indicated are for trend across quartiles. FIG. 4C shows odds ratio and 95% confidence interval for TMANO levels as a predictor for CVD, CAD, PAD and CAD+PAD risks following multilogistic regression. The model consisted of Framingham risk score, estimated glomerular filtration rate determined by the MDRD formula, C-reactive protein (CRP) and TMANO levels.

FIGS. 5A-C provide the results of a case/control study examining the relationship between plasma abundance of TMANO and prospective risk for major adverse cardiac event (MACE; one or more of the following conditions: non-fatal MI, stroke, need for revascularization (revascularization) or death). FIG. 5A shows plasma TMANO in subjects who did (n=374) and did not (n=619) experience subsequent clinical events. FIG. 5B shows frequency of clinical events (revascularization, MI or stroke, death, and the composite, MACE) according to quartiles of TMANO abundance. P values indicated are for the trend across quartiles. FIG. 5C shows odds ratio and 95% confidence interval versus TMANO quartiles for incident risk of clinical events (need for revascularization, nonfatal MI or stroke, death or the composite, MACE) following multilogistic regression. The model consisted of Framingham risk score, estimated glomerular filtration rate by MDRD formula, C-reactive protein (CRP) and TMANO.

DETAILED DESCRIPTION OF THE INVENTION

Figure 1A:
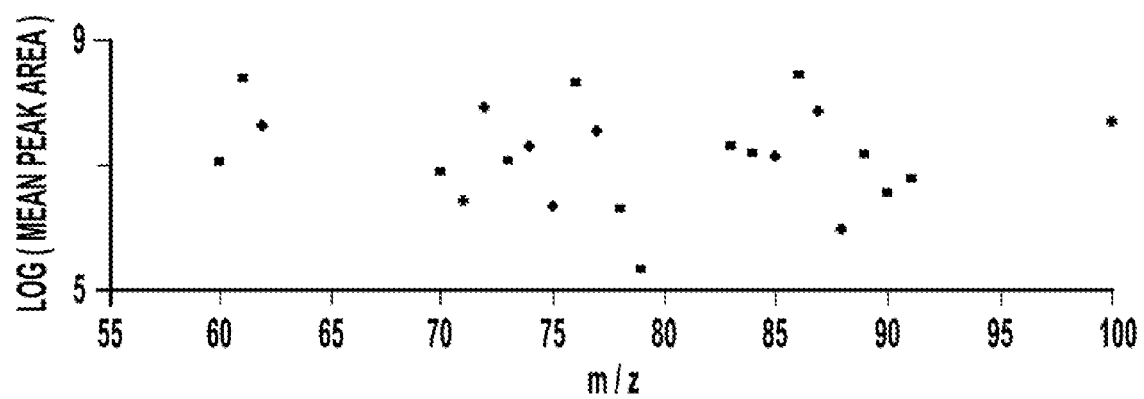
FIGS. 1A-C provide graphs showing a peak area of extracted ion chromatograms in positive-ion MS1 mode at m/z ranging from 50 to 100. The component with m/z=76 was identified as TMANO (trimethylamine N-oxide) by reverse phase high performance liquid chromatography (HPLC) coupled to a mass spectrometer. The top panel (FIG. 1A) indicates magnitude of the signal. The middle panel (FIG. 1B) shows the −logP value of levels in the 4th vs 1st quartile for each analyte in this m/z range. The bottom panel (FIG. 1C) indicates the odds ratio (95% confidence interval) for analytes in this m/z range for 4th quartile vs 1st quartile levels of each analyte.

In one embodiment, the present invention provides methods and markers for characterizing a subject's, particularly a human subject's, risk of having cardiovascular disease, particularly atherosclerotic cardiovascular disease. In another embodiment, the present invention provides methods of characterizing a subject's risk of developing cardiovascular disease. In another embodiment, the present invention provides methods for characterizing a subject's risk of experiencing a complication of cardiovascular disease (CVD) or an adverse cardiac event within the ensuing year, 2 years, or 3 years. In another embodiment, the present invention provides a method for determining whether a subject presenting with chest pain is at risk of experiencing a heart attack or other major adverse cardiac event within the ensuing month, six months, or year. The present methods are especially useful for identifying those subjects who are in need of highly aggressive CVD therapies as well as those subjects who require no therapies targeted at inhibiting or preventing CVD or complications of CVD.

As used herein, the term "diagnosis" can encompass determining the nature of disease in a subject, as well as determining the severity and probable outcome of disease or episode of disease and/or prospect of recovery (prognosis). "Diagnosis" can also encompass diagnosis in the context of rational therapy, in which the diagnosis guides therapy, including initial selection of therapy, modification of therapy (e.g., adjustment of dose and/or dosage regimen), and the like.

The terms "individual," "host," "subject," and "patient" are used interchangeably herein, and generally refer to a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. Diagnosis of humans is of particular interest.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a sample" includes a plurality of such samples and reference to a choline-related trimethylamine containing compound includes reference to one or more choline-related trimethylamine containing compounds and equivalents thereof known to those skilled in the art, and so forth.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values; however, inherently contain certain errors necessarily resulting from error found in their respective measurements.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In one embodiment, the present methods include determining the levels of choline-related trimethylamine-containing compounds in a biological sample (e.g., a bodily fluid obtained from a subject). Such choline-related trimethylamine-containing compounds include betaine, trimethylamine-N-oxide, choline, known equivalents and metabolites thereof. In one embodiment, the methods include determining the levels of one or more of the three compounds TMANO, choline, and betaine. In an additional embodiment, the present methods comprise determining the levels TMANO in a biological sample. In another embodiment, the methods comprise determining levels of choline, betaine, or both in a biological sample from the subject.

In certain embodiments, levels of TMANO, choline, betaine, or any combination thereof in a biological sample from the subject are compared to a corresponding control value or values that are derived from measurements of TMANO, choline, betaine, or any combination thereof in comparable biological samples obtained from a reference cohort. Corresponding values, as used herein, refer to use of an appropriate control for a given compound, such as determining the reference population levels of TMANO to use as a control value for comparison to TMANO levels determined in a subject. Levels of TMANO, choline, betaine, or any combination thereof in a biological sample obtained from a subject, alternatively, may be compared to levels of an internal standard in the biological sample obtained from the subject. As is known to those skilled in the art, internal standards can be a variety of compounds, typically similar to the target analyte, that are present in a known amount and help quantify the analyte in a sample. For example, internal standards that can be used to quantify choline include acetyl-.beta.-methylcholine and butyrylcholine. In certain embodiments, the biological sample is blood, or a fluid derived from blood, e.g. serum, plasma, etc.

In one embodiment, the comparison characterizes a subject's risk of having CVD, as determined using standard protocols for diagnosing CVD. Further embodiments are directed to characterizing the present risk of having atherosclerotic CVD. Moreover, the extent of the difference between the subject's TMANO, choline, and/or betaine levels and the control value is also useful for characterizing the extent of the risk and thereby, determining which subjects would most greatly benefit from certain therapies. More specifically, there may be a positive correlation between the difference and the extent of the risk such that a large difference in levels corresponds to a large amount of risk.

In another embodiment, the comparison characterizes the subject's risk of developing CVD in the future. As illustrated in Example 2 herein, choline-related trimethylamine-containing compounds have prognostic utility for identifying the likelihood that a subject will develop CVD. While not intending to be bound by theory, there appears to be a link between choline metabolism, gut flora involved in choline metabolism, and the risk for developing CVD and/or a major adverse cardiac event.

For example, the comparison of the amount of choline-related trimethylamine-containing compounds in a subject to control values can be used to characterize the subject's risk of experiencing a major adverse cardiac event within the ensuing, three years, or in certain embodiments, two years, or in certain embodiments, one year. The present methods can also be used to determine if a subject presenting with chest pain is at risk of experiencing an adverse cardiac event, such as a myocardial infarction, reinfarction, the need for revascularization, and/or death, near term. In this context, the term "near term" means within the following day, 3 months, 6 months, or year after the subject presents with chest pain.

Also provided herein are methods for monitoring over time the status of CVD in a subject. Further embodiments are directed to monitoring over time the status of atherosclerotic CVD. In one embodiment, the method comprises determining the levels of TMANO, choline, and/or betaine in a biological sample taken from the subject at an initial time and in a corresponding biological sample taken from the subject at a subsequent time. An increase in levels of TMANO, choline, and/or betaine in a biological sample taken at the subsequent time as compared to the initial time indicates that a subject's risk of having CVD has increased. A decrease in levels of TMANO, choline, and/or betaine indicates that the subject's risk of having CVD has decreased. For those subjects who have already experienced an acute adverse cardiovascular event such as a myocardial infarction or ischemic stroke, such methods are also useful for assessing the subject's risk of experiencing a subsequent acute adverse cardiovascular event. In such subjects, an increase in levels of TMANO, choline, and/or betaine indicates that the subject is at increased risk of experiencing a subsequent adverse cardiovascular event. A decrease in levels of TMANO, choline, and/or betaine in the subject over time indicates that the subject's risk of experiencing a subsequent adverse cardiovascular event has decreased.

In another embodiment, the present invention provides a method for characterizing a subject's response to therapy directed at stabilizing or regressing CVD, such as atherosclerotic CVD. The method comprises determining levels of choline-related trimethylamine-containing compounds (e.g., TMANO, choline, and/or betaine) in a biological sample taken from the subject prior to therapy and determining the level of TMANO, choline, and/or betaine in a corresponding biological sample taken from the subject during or following therapy. A decrease in levels of TMANO, choline, and/or betaine in the sample taken after or during therapy as compared to levels of TMANO, choline, and/or betaine in the sample taken before therapy is indicative of a positive effect of the therapy on cardiovascular disease in the treated subject.

In another embodiment, the present invention relates to kits that include reagents for assessing levels of TMANO, choline, and/or betaine in biological samples obtained from a test subject. In certain embodiments, the kits also include printed materials such as instructions for practicing the present methods, or information useful for assessing a test subject's risk of CVD. Examples of such information include, but are not limited to cut-off values, sensitivities at particular cut-off values, as well as other printed material for characterizing risk based upon the outcome of the assay. In some embodiments, such kits may also comprise control reagents, e.g. known amounts of TMANO, choline, and/or betaine.

In certain embodiments, levels of choline-related trimethylamine-containing compounds (e.g., TMANO, choline, and/or betaine) in a biological sample of the test subject are compared to a control value that is derived from levels of TMANO, choline, and/or betaine in comparable biological samples of control subjects. In an alternative embodiment, levels of TMANO, choline, and/or betaine in the biological sample of the test subject may then be compared to an internal standard based on levels of other biomolecules in the subject's biological sample. Test subjects whose levels of TMANO, choline, and/or betaine are above the control value or in the higher range of control values are at greater risk of having or developing cardiovascular disease than test subjects whose levels of TMANO, choline, and/or betaine are at or below the control value or in the lower range of control values. Moreover, the extent of the difference between the subject's TMANO, choline, and/or betaine levels and the control value is also useful for characterizing the extent of the risk and thereby, determining which subjects would most benefit from certain therapies.

In certain embodiments, the subject's risk profile for CVD is determined by combining a first risk value, which is obtained by comparing levels of choline-related trimethylamine-containing compounds (e.g., TMANO, choline, and/or betaine) in a biological sample of the subject with levels of TMANO, choline, and/or betaine in a control population, with one or more additional risk values to provide a final risk value. Such additional risk values may be obtained by procedures including, but not limited to, determining the subject's blood pressure, assessing the subject's response to a stress test, determining levels of myeloperoxidase, homocitrulline, nitrotyrosine, C-reactive protein, low density lipoprotein, or cholesterol in a bodily sample from the subject, or assessing the subject's atherosclerotic plaque burden.

In one embodiment, the method is used to assess the test subject's risk of having cardiovascular disease, and in particular atherosclerotic cardiovascular disease. Medical procedures for determining whether a human subject has coronary artery disease or is at risk for experiencing a complication of coronary artery disease include, but are not limited to, coronary angiography, coronary intravascular ultrasound (IVUS), stress testing (with and without imaging), assessment of carotid intimal medial thickening, carotid ultrasound studies with or without implementation of techniques of virtual histology, coronary artery electron beam computer tomography (EBTC), cardiac computerized tomography (CT) scan, CT angiography, cardiac magnetic resonance imaging (MM), and magnetic resonance angiography (MRA). Because cardiovascular disease is typically not limited to one region of a subject's vasculature, a subject who is diagnosed as having or being at risk of having coronary artery disease is also considered at risk of developing or having other forms of CVD such as cerebrovascular disease, aortic-iliac disease, and peripheral artery disease. Subjects who are at risk of having cardiovascular disease are at risk of having an abnormal stress test or abnormal cardiac catheterization. Subjects who are at risk of having CVD are also at risk of exhibiting increased carotid intimal medial thickness and coronary calcification, characteristics that can be assessed using non-invasive imaging techniques. Subjects who are at risk of having CVD are also at risk of having an increased atheroscleorotic plaque burden, a characteristic that can be examined using intravascular ultrasound.

In another embodiment, the present methods are used to assess a subject's risk of developing cardiovascular disease in the future. In one embodiment, the subject is an apparently healthy individual. In another embodiment, the subject is not otherwise at an elevated risk of having cardiovascular disease.

Embodiments of the present methods can also be used to assess the test subject's risk of experiencing an adverse cardiac event within the ensuing three years, two years, or year. In another embodiment, the present methods are used to determine if a subject presenting with chest pain is at risk of experiencing a heart attack or other major adverse cardiac event, such as a near term myocardial infarction, reinfarction, the need for revascularization, or death. As used in this context, the term "near term" means within one year. Thus, subjects who are at near term risk may be at risk of experiencing a major adverse cardiac event within the following day, 3 months, or 6 months after presenting with chest pain.

The present invention also provides a method for monitoring over time the status of CVD in a subject who has been diagnosed as having CVD. In this context, the method is also useful for monitoring the risk for atherosclerotic progression or regression in a subject with CVD. In one embodiment, the method comprises determining the levels of TMANO, choline, and/or betaine in a biological sample taken from the subject at an initial time and in a corresponding biological sample taken from the subject at a subsequent time. An increase in levels of choline-related trimethylamine-containing compounds (e.g., TMANO, choline, and/or betaine) in a biological sample taken at the subsequent time as compared to the initial time indicates that the subject's CVD has progressed or worsened. A decrease in levels of TMANO, choline, and/or betaine indicates that the CVD has improved or regressed. For those subjects who have already experienced an acute adverse cardiovascular event such as a myocardial infarction or ischemic stroke, such methods can also be used to assess the subject's risk of having a subsequent acute adverse cardiovascular event. An increase over time in levels of the TMANO, choline, and/or betaine in the subject indicates that a subject's risk of experiencing a subsequent adverse cardiovascular event has increased. A decrease over time in levels of TMANO, choline, and/or betaine in the subject indicates that that the subject's risk of experiencing a subsequent adverse cardiovascular event has decreased.

In another embodiment, the present invention provides a method for evaluating therapy in a subject suspected of having or diagnosed as having cardiovascular disease. The method comprises determining levels one or more choline-related trimethylamine-containing compounds (e.g., TMANO, choline, and/or betaine) in a biological sample taken from the subject prior to therapy and determining levels of TMANO, choline, and/or betaine in a corresponding biological sample taken from the subject during or following therapy. A decrease in levels of TMANO, choline, and/or betaine in the sample taken after or during therapy as compared to levels of TMANO, choline, and/or betaine in the sample taken before therapy is indicative of a positive effect of the therapy on cardiovascular disease in the treated subject.

Biological Samples

Biological samples include, but are not necessarily limited to bodily fluids such as blood-related samples (e.g., whole blood, serum, plasma, and other blood-derived samples), urine, cerebral spinal fluid, bronchoalveolar lavage, and the like. Another example of a biological sample is a tissue sample. TMANO, choline, and/or betaine levels can be assessed either quantitatively or qualitatively, usually quantitatively. The levels of the choline-related trimethylamine-containing compounds can be determined either in vivo or ex vivo.

A biological sample may be fresh or stored (e.g. blood or blood fraction stored in a blood bank). The biological sample may be a bodily fluid expressly obtained for the assays of this invention or a bodily fluid obtained for another purpose which can be subsampled for the assays of this invention.

In one embodiment, the biological sample is whole blood. Whole blood may be obtained from the subject using standard clinical procedures. In another embodiment, the biological sample is plasma. Plasma may be obtained from whole blood samples by centrifugation of anti-coagulated blood. Such process provides a buffy coat of white cell components and a supernatant of the plasma. In another embodiment, the biological sample is serum. Serum may be obtained by centrifugation of whole blood samples that have been collected in tubes that are free of anti-coagulant. The blood is permitted to clot prior to centrifugation. The yellowish-reddish fluid that is obtained by centrifugation is the serum. In another embodiment, the sample is urine.

The sample may be pretreated as necessary by dilution in an appropriate buffer solution, heparinized, concentrated if desired, or fractionated by any number of methods including but not limited to ultracentrifugation, fractionation by fast performance liquid chromatography (FPLC), or precipitation of apolipoprotein B containing proteins with dextran sulfate or other methods. Any of a number of standard aqueous buffer solutions at physiological pH, such as phosphate, Tris, or the like, can be used.

Subjects

The subject is any human or other animal to be tested for characterizing its risk of CVD. In certain embodiments, the subject does not otherwise have an elevated risk of an adverse cardiovascular event. Subjects having an elevated risk of an adverse cardiovascular event include those with a family history of cardiovascular disease, elevated lipids, smokers, prior acute cardiovascular event, etc. (See, e.g., Harrison's Principles of Experimental Medicine, 15th Edition, McGraw-Hill, Inc., N.Y.—hereinafter "Harrison's").

In certain embodiments the subject is apparently healthy. "Apparently healthy", as used herein, describes a subject who does not have any signs or symptoms of CVD or has not previously been diagnosed as having any signs or symptoms indicating the presence of atherosclerosis, such as angina pectoris, history of an acute adverse cardiovascular event such as a myocardial infarction or stroke, evidence of atherosclerosis by diagnostic imaging methods including, but not limited to coronary angiography.

In certain embodiments, the subject is a nonsmoker. "Nonsmoker" describes an individual who, at the time of the evaluation, is not a smoker. This includes individuals who have never smoked as well as individuals who have smoked but have not used tobacco products within the past year. In certain embodiments, the subject is a smoker.

In some embodiments, the subject is a nonhyperlipidemic subject. "Nonhyperlipidemic" describes a subject that is a nonhypercholesterolemic and/or a nonhypertriglyceridemic subject. A "nonhypercholesterolemic" subject is one that does not fit the current criteria established for a hypercholesterolemic subject. A nonhypertriglyceridemic subject is one that does not fit the current criteria established for a hypertriglyceridemic subject (See, e.g., Harrison's Principles of Experimental Medicine, 15th Edition, McGraw-Hill, Inc., N.Y.—hereinafter "Harrison's"). Hypercholesterolemic subjects and hypertriglyceridemic subjects are associated with increased incidence of premature coronary heart disease. A hypercholesterolemic subject has an LDL level of >160 mg/dL, or >130 mg/dL and at least two risk factors selected from the group consisting of male gender, family history of premature coronary heart disease, cigarette smoking (more than 10 per day), hypertension, low HDL (<35 mg/dL), diabetes mellitus, hyperinsulinemia, abdominal obesity, high lipoprotein (a), and personal history of cerebrovascular disease or occlusive peripheral vascular disease. A hypertriglyceridemic subject has a triglyceride (TG) level of >250 mg/dL. Thus, a nonhyperlipidemic subject is defined as one whose cholesterol and triglyceride levels are below the limits set as described above for both the hypercholesterolemic and hypertriglyceridemic subjects.

Methods for Measuring Levels of Choline-Related Trimethylamine-Containing Compounds The levels of choline-related trimethylamine-containing compounds can be measured using any suitable analytic method, including standard methods known in the art. For example, the levels of TMANO, choline, and betaine in a subject can be measured using an analytic device, which is a machine including a detector capable of identifying small organic molecules such as choline-related trimethylamine-containing compounds. The analytic device may be a spectrometric device, such as a mass spectrometer, an ultraviolet spectrometer, or a nuclear magnetic resonance spectrometer. A spectrometer is a device that uses a spectroscopic technique to assess the concentration or amount of a given species in a medium such as a biological sample (e.g., a bodily fluid). The analytic device used to measure the levels of choline-related trimethylamine-containing compounds can be either a portable or a stationary device. In addition to including equipment used for detecting the choline-related trimethylamine-containing compounds, the analytic device can also include additional equipment to provide physical separation of analytes prior to analysis. For example, if the analyte detector is a mass spectrometer, it may also include a high performance liquid chromatograph (HPLC) or gas chromatograph (GC) to purify the choline-related trimethylamine-containing compounds before their detection by mass spectrometry.

As indicated herein, mass spectrometry-based methods can be used to assess levels of TMANO, choline, and/or betaine in a biological sample. Mass spectrometers include an ionizing source (e.g., electrospray ionization), an analyzer to separate the ions formed in the ionization source according to their mass-to-charge (m/z) ratios, and a detector for the charged ions. In tandem mass spectrometry, two or more analyzers are included. Such methods are standard in the art and include, for example, HPLC with on-line electrospray ionization (ESI) and tandem mass spectrometry.

Other spectrometric methods can also be used to detect choline-related trimethylamine-containing compounds. For example, choline-related trimethylamine-containing compounds can be measured by HPLC using a variety of detectors including, but not limited to UV or Vis (of a derivatized form), mass spectrometry, or GC/MS. Another method that can be used to identify choline-related trimethylamine-containing compounds is nuclear magnetic resonance (NMR).

Examples of NMR Include Proton NMR and Carbon-13 NMR

Once the levels of choline-related trimethylamine-containing compounds have been determined, they can be displayed in a variety of ways. For example, the levels of choline-related trimethylamine-containing compounds can be displayed graphically on a display as numeric values or proportional bars (i.e., a bar graph) or any other display method known to those skilled in the art. The graphic display can provide a visual representation of the amount of the choline-related trimethylamine-containing compound (e.g., TMANO, choline, or betaine) in the biological sample being evaluated. In addition, in some embodiments, the analytic device can also be configured to display a comparison of the levels of TMANO in the subject's bodily fluid to a control value based on levels of TMANO in comparable bodily fluids from a reference cohort.

Control Value

In certain embodiments, levels of TMANO, choline, and/or betaine in the biological sample obtained from the test subject may compared to a control value. A control value is a concentration of an analyte that represents a known or representative amount of an analyte. For example, the control value can be based upon levels of TMANO, choline, and/or betaine in comparable samples obtained from a reference cohort. In certain embodiments, the reference cohort is the general population. In certain embodiments, the reference cohort is a select population of human subjects. In certain embodiments, the reference cohort is comprised of individuals who have not previously had any signs or symptoms indicating the presence of atherosclerosis, such as angina pectoris, history of an acute adverse cardiovascular event such as a myocardial infarction or stroke, evidence of atherosclerosis by diagnostic imaging methods including, but not limited to coronary angiography. In certain embodiments, the reference cohort includes individuals, who if examined by a medical professional would be characterized as free of symptoms of disease (e.g., cardiovascular disease). In another example, the reference cohort may be individuals who are nonsmokers (i.e., individuals who do not smoke cigarettes or related items such as cigars). A nonsmoker cohort may have a different normal range of TMANO, choline, and/or betaine than will a smoking population or the general population. Accordingly, the control values selected may take into account the category into which the test subject falls. Appropriate categories can be selected with no more than routine experimentation by those of ordinary skill in the art.

The control value is preferably measured using the same units used to characterize the level of TMANO, choline, and/or betaine obtained from the test subject. Thus, if the level of the TMANO is an absolute value such as the units of TMANO, choline, and/or betaine per ml of blood, the control value is also based upon the units of TMANO, choline, and/or betaine per ml of blood in individuals in the general population or a select population of human subjects.

The control value can take a variety of forms. The control value can be a single cut-off value, such as a median or mean. The control value can be established based upon comparative groups such as where the risk in one defined group is double the risk in another defined group. The control values can be divided equally (or unequally) into groups, such as a low risk group, a medium risk group and a high-risk group, or into quadrants, the lowest quadrant being individuals with the lowest risk the highest quadrant being individuals with the highest risk, and the test subject's risk of having CVD can be based upon which group his or her test value falls. Control values of TMANO in biological samples obtained, such as mean levels, median levels, or "cut-off" levels, are established by assaying a large sample of individuals in the general population or the select population and using a statistical model such as the predictive value method for selecting a positivity criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co. Malvern, Pa., which is specifically incorporated herein by reference. A "cutoff" value can be determined for each risk predictor that is assayed.

Comparison of a Choline-Related Trimethylamine-Containing Compound Obtained from a Subject to a Control Value Levels of TMANO, choline, and/or betaine in a subject's biological sample may be compared to a single control value or to a range of control values. If the level of the present risk predictor in the test subject's biological sample is greater than the control value or exceeds or is in the upper range of control values, the test subject is at greater risk of developing or having CVD or experiencing an adverse cardiac event within the ensuing year, two years, and/or three years than individuals with levels comparable to or below the control value or in the lower range of control values. In contrast, if levels of the present risk predictor in the test subject's biological sample is below the control value or is in the lower range of control values, the test subject is at a lower risk of developing or having CVD or experiencing an adverse cardiac event within the ensuing year, two years, and/or three years than individuals whose levels are comparable to or above the control value or exceeding or in the upper range of control values. The extent of the difference between the test subject's risk predictor levels and control value is also useful for characterizing the extent of the risk and thereby determining which individuals would most greatly benefit from certain aggressive therapies. In those cases, where the control value ranges are divided into a plurality of groups, such as the control value ranges for individuals at high risk, average risk, and low risk, the comparison involves determining into which group the test subject's level of the relevant risk predictor falls.

Another type of control value is an internal standard in the sample. An internal standard is a known amount of another compound that can be provided in a sample that can be measured along with the analyte to serve as a reference. The diagnostic methods described herein can also be carried out by determining the levels of TMANO, choline, and/or betaine in a subject's biological sample and comparing them to the amount of an internal standard.

Evaluation of CVD Therapeutic Agents

Also provided are methods for evaluating the effect of CVD therapeutic agents on individuals who have been diagnosed as having or as being at risk of developing CVD. Such therapeutic agents include, but are not limited to, anti-inflammatory agents, insulin sensitizing agents, antihypertensive agents, anti-thrombotic agents, anti-platelet agents, fibrinolytic agents, lipid reducing agents, direct thrombin inhibitors, ACAT inhibitor, CDTP inhibitor thioglytizone, glycoprotein receptor inhibitors, agents directed at raising or altering HDL metabolism such as ApoA-I Milano or CETP inhibitors (e.g., torcetrapib), or agents designed to act as artificial HDL. Accordingly, a CVD therapeutic agent, as used herein, refers to a broader range of agents that can treat a range of cardiovascular-related conditions, and may encompass more compounds than the traditionally defined class of cardiovascular agents.

Evaluation of the efficacy of CVD therapeutic agents can include obtaining a predetermined value of the choline-related trimethylamine-containing compound or compounds in a biological sample, and determining the level of one or more choline-related trimethylamine-containing compounds in a corresponding biological fluid taken from the subject following administration of the therapeutic agent. A decrease in the level of one or more of the choline-related trimethylamine-containing compounds in the sample taken after administration of the therapeutic as compared to the level of the selected risk markers in the sample taken before administration of the therapeutic agent is indicative of a positive effect of the cardiovascular therapeutic agent on cardiovascular disease in the treated subject.

A predetermined value can be based on the levels of one or more choline-related trimethylamine-containing compounds in a biological sample taken from a subject prior to administration of a CVD therapeutic agent. In another embodiment, the predetermined value is based on the levels of one or more choline-related trimethylamine-containing compounds in comparable biological samples taken from control subjects that are apparently healthy, as defined herein.

Embodiments of the methods described herein can also be useful for determining if and when therapeutic agents that are targeted at preventing CVD or for slowing the progression of CVD should and should not be prescribed for an individual. For example, individuals with TMANO, choline, and/or betaine values above a certain cutoff value, or that are in the higher tertile or quartile of a "normal range," could be identified as those in need of more aggressive intervention with lipid lowering agents, life style changes, etc.

EXAMPLES

The following examples are for purposes of illustration only and are not intended to limit the scope of the claims.

Example 1

Based on the following studies, it was determined that levels of a compound called TMANO (trimethylamine-N-oxide) in a biological sample (e.g., plasma, serum, whole blood, or urine), can serve as a predictor of cardiovascular disease risk both for short term adverse outcomes, such as the evaluation of a patient presenting with chest pain, for near term evaluation, and for longer term outcomes for lower risk populations, such as those obtained in community based screenings, or in subjects undergoing elective diagnostic cardiovascular procedures like angiography, cardiac CT, stress testing, or myocardial perfusion studies.

TMANO levels predict the risk of having CVD, such as Coronary Artery Disease (CAD) and/or Peripheral Artery Disease (PAD), as well as the risk of experiencing a major adverse cardiac event including non-fatal myocardial infarction (MI), stroke, the need for revascularization, or death.

TMANO levels can also be used to monitor CVD therapies and the response to anti-inflammatory and other cardiovascular risk-reducing interventions.

TMANO was discovered through a series of metabolomics studies. An effort was made to define low molecular weight analytes in plasma, serum, blood or urine whose levels would predict cardiovascular disease (CVD). A "learning set" of 50% cases to 50% controls was used, where cases were defined by subjects who experience a major adverse cardiac event in the ensuing 3 year period, such as experiencing a non-fatal MI, stroke, revascularization event (CABG, angioplasty, stent) or death, and controls who were individuals lacking such events. Initial subjects examined were from a large clinical repository of sequential subjects undergoing elective diagnostic cardiac catheterization and for whom outcome data was available.

Initially, proteins were removed from plasma and the low molecular weight components (<1000) analyzed by Liquid Chromatography-Mass Spectrometry (LC/MS) analysis. Each analyte having a molecular weight eluting under 1000 was noted for retention time and m/z, and signal of ionization. The results obtained for the cases were then compared to those obtained for the controls.

Figure 1B:
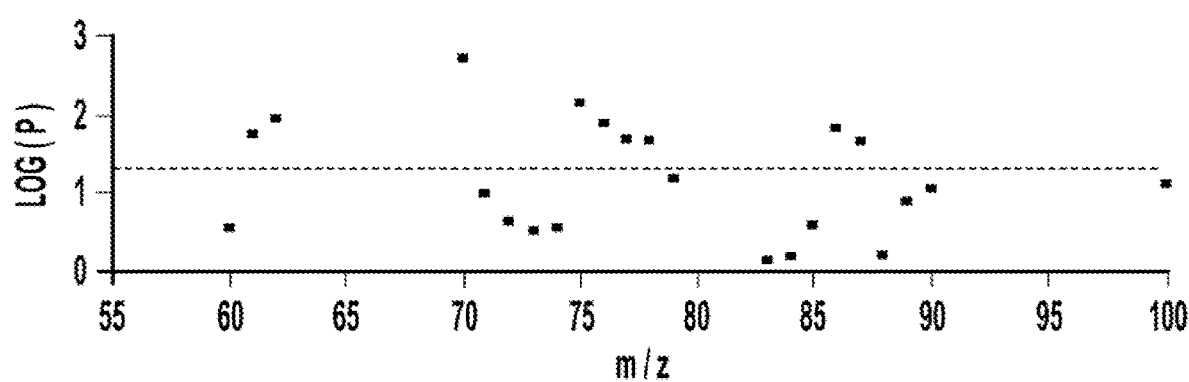
Figure 1C:
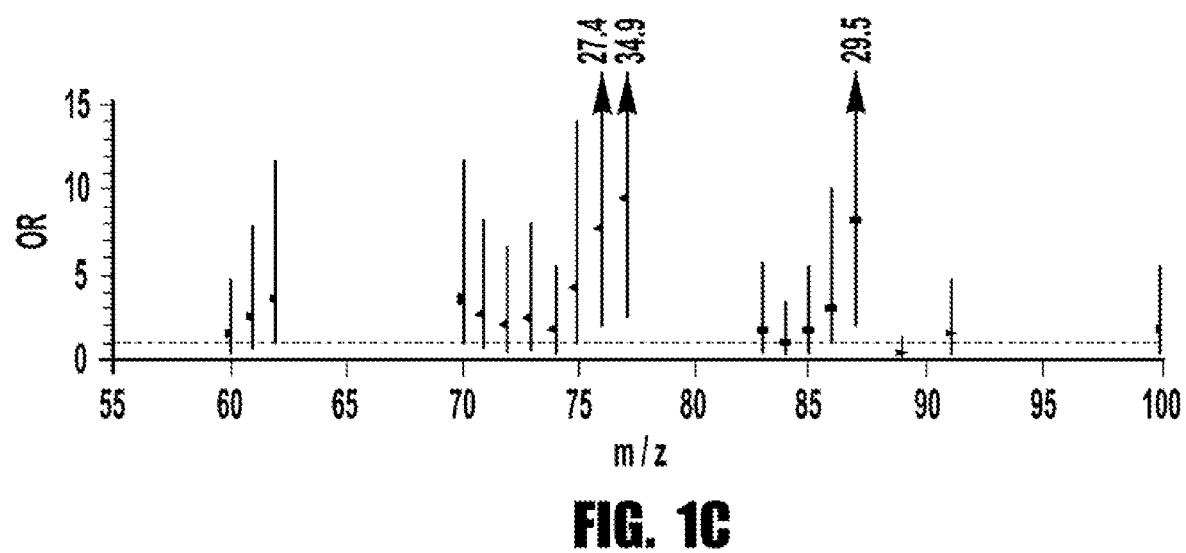

Shown in FIG. 1 is a plot of only the analytes monitored between m/z 50 and 100. The top panel (a) indicates magnitude of the signal. There was interest in identifying analytes in the plasma that could distinguish between cases and controls, and for which a large signal was seen. The middle panel (b) shows the −log P value of levels in the 4th vs 1st quartile for each analyte in this m/z range. These were evaluated to identify an analyte that was predictive of CVD risks, and thus had a significant P value (i.e., −log P>than 1.3, which corresponds to P<0.05). The bottom panel (c) indicates the odds ratio (95% confidence interval) for analytes in this m/z range for 4th quartile vs 1st quartile levels of each analyte. The analytes providing higher Odds Ratios (ORs) and Confidence Intervals (CIs) are significant. FIG. 1 shows several analytes that might be suitable to select between cases and controls. The identification of the analyte exhibiting m/z 76 was pursued because it showed a high signal, significant separation of cases from controls, and a large odds ratio for the prediction of adverse cardiac events.

The data provided in FIG. 1 was obtained by reverse phase HPLC coupled to API 365 triple quadrupole mass spectrometer (Applied Biosystems, Foster, Calif.) with Ionics EP 10+ upgrade (Concord) in positive ESI-MS ion mode. Plasma supernatant (20 µl) after precipitation with 80% methanol was injected onto a Phenyl column (4.6×250 mm, 5 pm Rexchrom Phenyl) (Regis) at a flow rate of 0.8 ml/min. The separation was performed using a gradient starting from 10 mM ammonium formate over 0.5 min, then to 5 mM ammonium formate, 25% methanol and 0.1% formic acid over 3 min, held for 8 min, followed by 100% methanol and water washing for 3 min each. The eluate in the initial 4 min from HPLC column was switched off, and only the eluate from 4 to 11 min was applied to data acquisition by mass spectrometer. With regard to panel (b), significant levels for the difference in each extracted ion between 50 controls who underwent diagnostic cardiac catheterization and failed to experience a major adverse cardiac event over the ensuing 3 years following study enrollment and 50 cases who experienced a major adverse cardiac event (MACE, the composite of non-fatal MI, stroke, need for revascularization or death) in the 3 year period following study enrollment. With regard to panel (c), the odds ratio of prospect risk for MACE, revascularization (Revasc), non-fatal MI or stroke, death, according to the extracted ion peak area, are provided. Odds ratio (ORs) and confidence intervals (CIs) were calculated using logistic regression models comparing the risk of the highest quartiles to the lowest quartile.

Figure 2A:
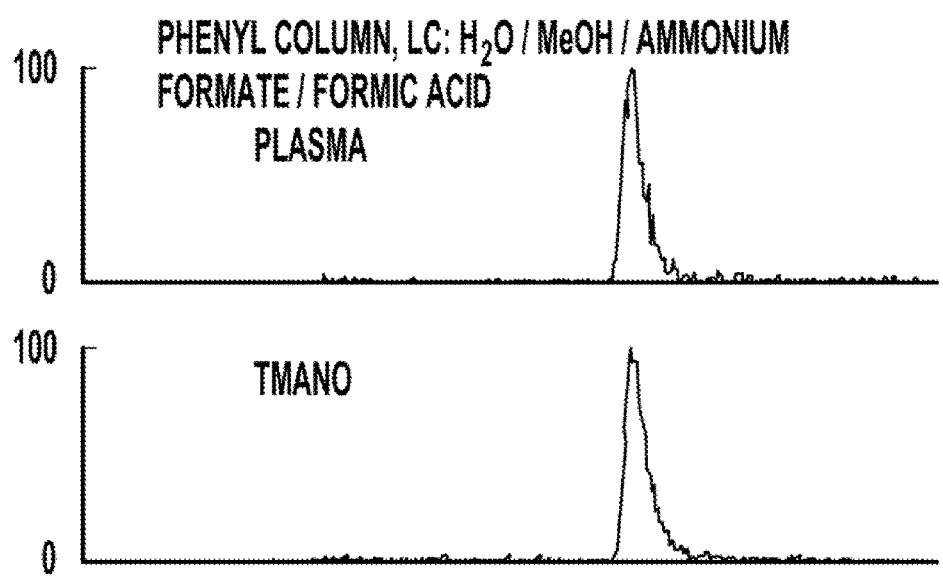
FIGS. 2A-C provides graphs showing the results of extracted ion chromatograms in positive-ion MS1 mode at m/z=76. The component with in/z=76 was identified by reverse phase HPLC coupled to a mass spectrometer. Plasma supernatant (20 µl) after precipitation with 80% methanol or 20 µl trimethylamine N-oxide (TMANO) stand was injected onto a Phenyl column (4.6×250 mm, 5 pm Rexchrom Phenyl) (Regis) at a flow rate of 0.8 ml/min (A-B) or Prodigy 5 u ODS (2) column (150×2.00 mm, 5 micron) at a flow rate of 0.2 ml/min (C). The separation in FIG. 2a was performed using a gradient starting from 10 mM ammonium formate over 0.5 min, then to 5 mM ammonium formate, 25% methanol and 0.1% formic acid over 3 min, held for 8 min, followed by 100% methanol and water washing for 3 min each. The separation in FIG. 2b was performed using a gradient starting from 0.1% formic acid over 2 min, then to 18% acetonitrile with 0.1% formic acid over 18 min, followed by 100% acetonitrile and water washing for 3 min each, starting from 0.1% formic acid over 2 min, then to 18% acetonitrile with 0.1% formic acid over 18 min, followed by 100% acetonitrile and water washing for 6 min each. The separation in FIG. 2C was performed using a gradient starting from 0.1% formic acid to 50% acetonitrile with 0.1% formic acid over 18 min, followed by 100% acetonitrile and water washing for 3 min each, starting from 0.1% formic acid over 2 min, then to 18% acetonitrile with 0.1% formic acid over 18 min, followed by 100% acetonitrile and water washing for 3 min each.
Figure 2B:
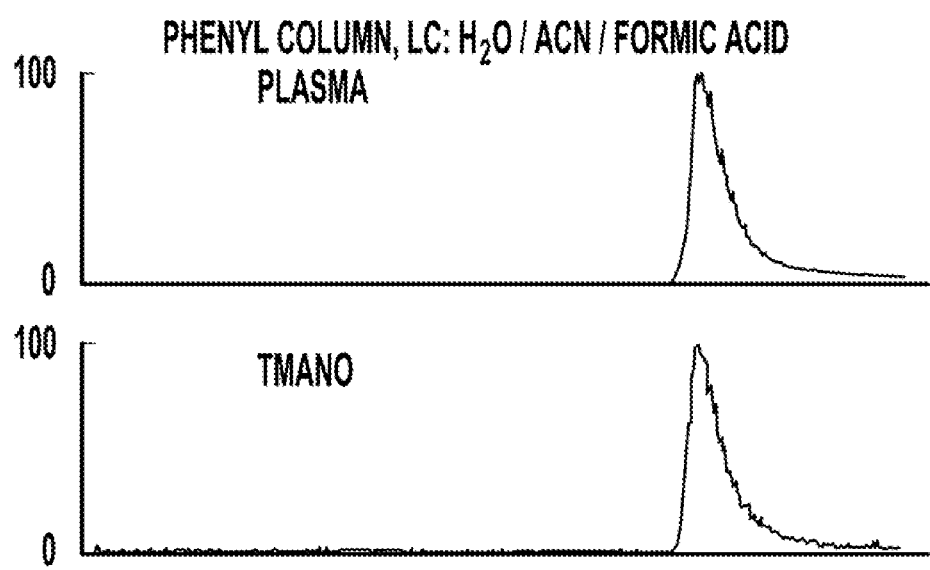
Figure 2C:
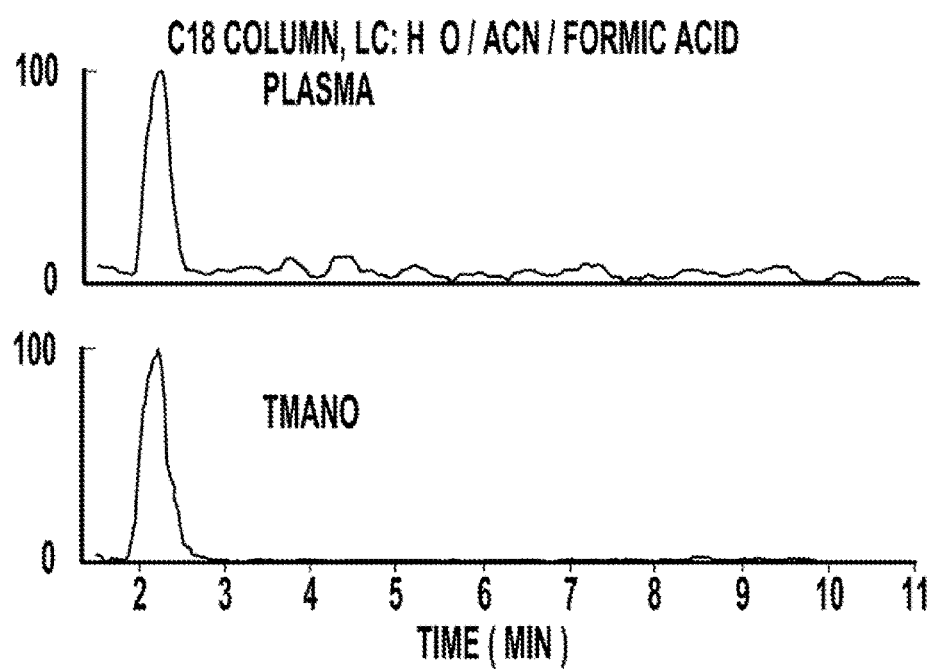

Shown in FIG. 2 are chromatographs indicating the analyte with m/z 76 in plasma that tracks with cardiac risk has similar chromatographic characteristics to TMANO in 3 separate column/mobile phase combinations, and that the analyte appears to be a single species, as evidenced by having a single peak.

The data provided in FIG. 2 was obtained by reverse phase HPLC coupled to API 365 triple quadrupole mass spectrometer (Applied Biosystems, Foster, Calif.) with Ionics EP 10+ upgrade (Concord) in positive ESI-MS ion mode. Plasma supernatant (20 µl) after precipitation with 80% methanol or 20 µl trimethylamine N-oxide (TMANO) stand was injected onto a Phenyl column (4.6×250 mm, 5 pm Rexchrom Phenyl) (Regis) at a flow rate of 0.8 ml/min(a-b) or Prodigy 5 u ODS (2) column (150×2.00 mm, 5 micron) at a flow rate of 0.2 ml/min (c). The separation in panel (a) was performed using a gradient starting from 10 mM ammonium formate over 0.5 min, then to 5 mM ammonium formate, 25% methanol and 0.1% formic acid over 3 min, held for 8 min, followed by 100% methanol and water washing for 3 min each. The separation in panel (b) was performed using a gradient starting from 0.1% formic acid over 2 min, then to 18% acetonitrile with 0.1% formic acid over 18 min, followed by 100% acetonitrile and water washing for 3 min each. starting from 0.1% formic acid over 2 min, then to 18% acetonitrile with 0.1% formic acid over 18 min, followed by 100% acetonitrile and water washing for 6 min each. The separation in panel (c) was performed using a gradient starting from 0.1% formic acid to 50% acetonitrile with 0.1% formic acid over 18 min, followed by 100% acetonitrile and water washing for 3 min each. starting from 0.1% formic acid over 2 min, then to 18% acetonitrile with 0.1% formic acid over 18 min, followed by 100% acetonitrile and water washing for 3 min each.

Table 1a provides conformation that the component isolated from plasma that tracks with incident CVD risks is TMANO and not another isomer with identical molecular weight and elemental composition. Note that only TMANO shows identical parent and daughter ions with retention time in 3 different solvent systems comparable to the analyte isolated from plasma that predicts CVD risks.

System 1: Regis RexChrom Phenyl HPLC column (25 cm×4.6 mm, 5 micron, 100 A). The separation was performed using gradient 0-0.5 min: 10 mM Ammonium formate; 0.5-3.5 min: linearly changed to 25% methanol with 5 mM ammonium formate and 0.1% formic acid and held for 8 min; 11.5-14 min: linearly changed to 100% methanol with 10 mM ammonium formate and held for 3 min; 17-20 min, 10 mM ammonium formate in water. The flow rate was 0.8 ml/min.

System 2: Regis RexChrom Phenyl HPLC column (25 cm×4.6 mm, 5 micron, 100 A). The separation was performed using gradient starting from 0.1% formic acid over 2 min, then to 18% acetonitrile with 0.1% formic acid over 18 min, followed by 100% acetonitrile and water washing for 3 min each. starting from 0.1% formic acid over 2 min, then to 18% acetonitrile with 0.1% formic acid over 18 min, followed by 100% acetonitrile and water washing for 6 min each. The flow rate was 0.8 ml/min.

System 3: Prodigy 5 u ODS (2) column (150×2.00 mm, 5 micron). The separation was performed using gradient starting from 0.1% formic acid to 50% acetonitrile with 0.1% formic acid over 18 min, followed by 100% acetonitrile and water washing for 3 min each, starting from 0.1% formic acid over 2 min, then to 18% acetonitrile with 0.1% formic acid over 18 min, followed by 100% acetonitrile and water washing for 3 min each. The flow rate was 0.2 ml/min.

Table 1b provides further independent conformation that the component isolated from plasma that tracks with incident CVD risks is TMANO and not another isomer with identical molecular weight and elemental composition. Note that only TMANO shows identical parent and daughter ions with retention time as the analyte isolated from plasma that predicts CVD risks. The isolated plasma component and the structures depicted of isomers with identical molecular weight and elemental composition were analyzed by GC MS following two distinct derivatization strategies. The results of Tables 1a and 1b unambiguously identify the isolated plasma component that predicts incident CVD risk as TMANO.

TABLE 1a

LC-MS characteristics of the positive protonated parental ion at m/z = 76

| Component | Structure | MH+ | System 1 RT (min) | System 1 Product-ions | System 2 RT (min) | System 2 Product ions | System 3 RT (min) | System 3 Product ions |
|---|---|---|---|---|---|---|---|---|
| Component Purified from Plasma | | 76.1097 | 7.6 | 58, 59 | 8.4 | 58, 59 | 1.8 | 58, 59 |
| TMANO | $(CH_3)_3N \rightarrow O$ | 76.1097 | 7.6 | 58, 59 | 8.4 | 58, 59 | 1.8 | 58, 59 |
| 1-Amino-2-propanol | $H_2NCH_2CH(OH)CH_3$ | 76.1097 | 6.0 | 58, 59 | 6.2 | 58, 59 | 1.8 | 58, 59 |
| 2-Amino-1-propanol | $CH_3CH(NH_2)CH_2OH$ | 76.1097 | 6.0 | 58, 59 | 6.2 | 58, 59 | 1.8 | 58, 59 |
| 3-Amino-1-propanol | $H_2NCH_2CH_2CH_2OH$ | 76.1097 | 6.0 | 58, 59 | 6.2 | 58, 59 | 1.8 | 58, 59 |
| Methyl-aminoethanol | $CH_3NHCH_2CH_2OH$ | 76.1097 | 6.5 | 58 | 6.7 | 58 | 1.8 | 58 |
| Glycolamide | $HOCH_2CONH_2$ | 76.1097 | 4.2 | 58 | 4.1 | 58 | 2.2 | 58 |
| Hydroxy-guanidine | $HONHC(=NH)NH_2$ | 76.1097 | 5.7 | 58, 59 | 5.8 | 58, 59 | 1.8 | 58, 59 |
| Glycine | $H_2NCH_2COOH$ | 76.1097 | 3.2 | 58, 59 | 2.0 | 59 | 2.5 | 59 |
| N-Isopropyl-hydroxylamine | $(CH_3)_2CHNOH$ | 76.1097 | 3.0 | 58 | 2.1 | 58, 59 | 1.9 | 59 |

TABLE 1b

GC-MS analysis of the peak from plasma that predicts incident CVD risks, and compounds with the same molecular weight of 75 (M+ = 76). All compounds were derivatized by trimethylchlorosilane (TMCS, system 1) or tricholoroethyl chloroformate (TCECF, system 2)

| | | System 1 | | System 2 | |
|---|---|---|---|---|---|
| Component | Structure | Derivative | RT (min) | Derivative | RT (min) |
| Component Purified from Plasma | | ND | | N,N-dimthyl trichloroethylcarbmate | 4.3 |
| TMANO | $(CH_3)_3N?O$ | ND | | N,N-dimthyl trichloroethylcarbmate | 4.3 |
| 1-Amino-2-propanol | $H_2NCH_2CH(OH)CH_3$ | TMS— | 4.4 | ND | |
| 2-Amino-I-propanol | $CH_3CH(NH_2)CH_2OH$ | DiTMS— | 3.8 | ND | |
| 3-Amino-I-propanol | $H_2NCH_2CH_2CH_2OH$ | DiTMS— | 3.7 | ND | |
| Methyl-aminoethanol | $CH_3NHCH_2CH_2OH$ | TMS— | 5.2 | ND | |
| Glycolamide | $HOCH_2CONH_2$ | DiTMS— | 5.3 | ND | |
| Hydroxy-guanidine | $HONHC(=NH)NH_2$ | TMS— | 4.3 | ND | |
| Glycine | $H_2NCH_2COOH$ | TriTMS— | 5.3 | ND | |
| N-Isopropyl-hydroxylamine | $(CH_3)_2CHNOH$ | TMS— | 4.3 | ND | |

System 1, the components reacted with Sylon HTP kit (Supelco, LB44596) containing HMDS, TMCS, Pyridine at 90° C. for 9 hours. GC-MS analysis of the TMS derivatives was performed on a Hewlett Packard (Palo Alto, Calif) 5973 mass spectrometer coupled to a Hewlett Packard 6890 gas chromatograph using the positive ion chemical ionization mode with methane as the reagent gas. The source temperature was set at 250° C. The TMS derivatives were separated on a J&W Scientific (Folsom, Calif.) DB-1 column (20.0 m, 0.18 mm inner diameter, 0.18-pm film thickness). The injector and the transfer line temperatures were maintained at 320° C. The GC oven was maintained at 60° C. for 2 min, increased at a rate of 20° C./min to 300° C.

System 2, the components was reacted with titanium (III) chloride and then with tricholoroethyl chloroformate (TCECF). The product was dissolved in toluene. GC-MS analysis of the TMS derivatives was performed on a Hewlett Packard (Palo Alto, Calif.) 5973 mass spectrometer coupled to a Hewlett Packard 6890 gas chromatograph using the positive ion chemical ionization mode with methane as the reagent gas. The source temperature was set at 250° C. The TMS derivatives were separated on an Agilent HP-1 Methyl Siloxane column (12.0 m, 0.20 mm inner diameter, 0.33-ttm film thickness). The injector and the transfer line temperatures were maintained at 250° C. The GC oven was maintained at 70° C. for 2 min, increased at a rate of 25° C./min to 170° C.

Figure 3A:
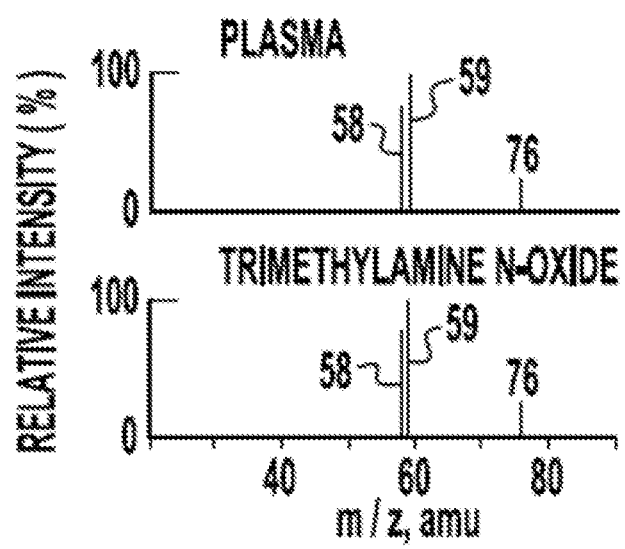
FIG. 3A provides collision (energy 21 eV)-induced dissociation (CID) mass spectra corresponding to the peak of m/z=76 in extracted ion chromatogram in positive MS1 mode in plasma supernatant and TMANO standard.
Figure 3B:
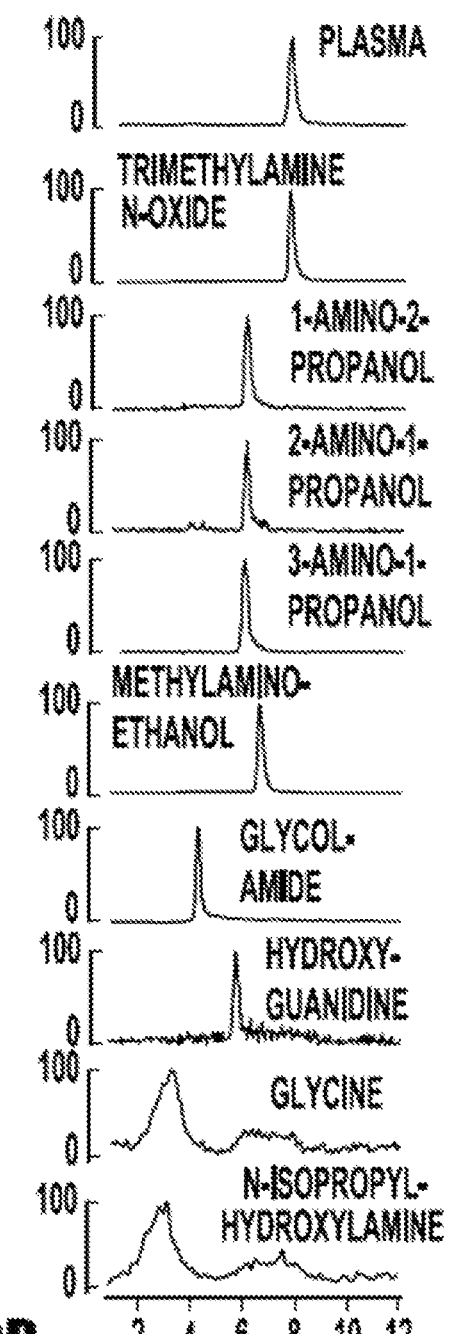
FIGS. 3B-3C provide extracted ion chromatograms in positive-ion multiple reaction monitoring (MRM) mode in mobile phase A (FIG. 3B) and B (FIG. 3C).
Figure 3C:
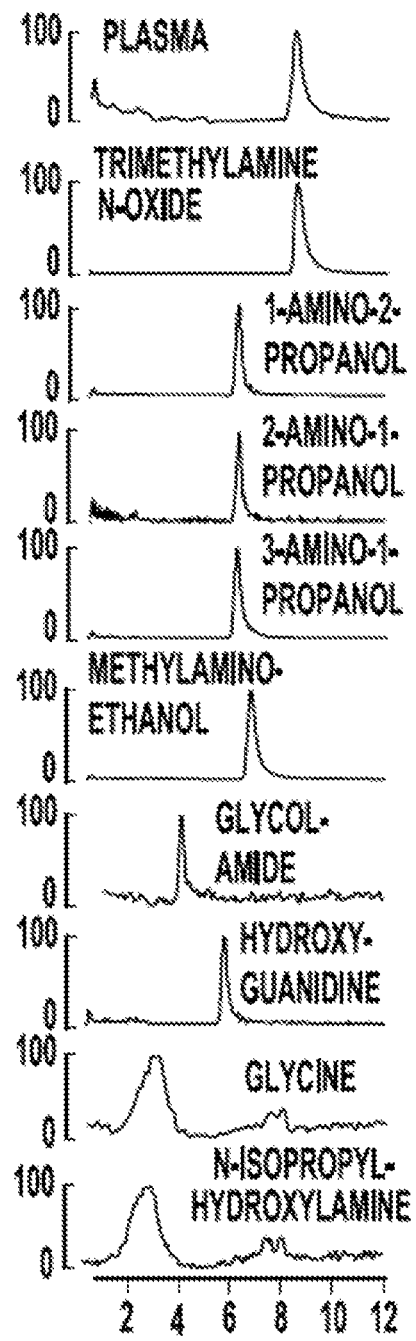

FIGS. 3A-C provide illustrative data confirming that TMANO is identical to the plasma component with m/z 76 that predicts incident CVD risks. FIG. 3A shows the CID spectrum of the plasma component and TMANO are identical. FIGS. 3B-3C show that the retention time of characteristic parent→daughter ion transitions for the plasma component are identical to TMANO in two distinct HPLC chromatographic systems, and that the other species in plasma with identical molecular weight can be distinguished from TMANO and do not share all properties with the isolated plasma component.

The data provided in FIG. 3A was obtained using collision (energy 21 eV) induced dissociation (CID) mass spectra corresponding to the peak of m/z=76 in extracted ion chromatogram in positive MS1 mode in plasma supernatant and TMANO standard. The data provided in FIGS. 3B-3C was obtained by extracted ion chromatograms in Mobile phase A and Mobile phase B. The Mobile phase A (FIG. 3B) extracted ion chromatograms in positive-ion multiple reaction monitoring (MRM) mode show parent-to-daughter transition of 76→58. For Mobile phase A, the sample (20 μl) was injected onto a Phenyl column (4.6×250 mm, 5 μm Rexchrom Phenyl) (Regis) at a flow rate of 0.8 ml/min. The separation was performed using a gradient starting from 10 mM ammonium formate over 0.5 min, then to 5 mM ammonium formate, 25% methanol and 0.1% formic acid over 3 min, held for 8 min, followed by 100% methanol and water washing for 3 min each. The Mobile phase B extracted ion chromatograms in positive MRM mode show parent-to-daughter transition of 76→58 except 765→9 for glycine. For Mobile phase B, the sample (20 μl) was injected onto a Phenyl column (4.6×250 mm, 5 μm Rexchrom Phenyl) (Regis) at a flow rate of 0.8 ml/min. The separation was performed using a gradient starting from 0.1% formic acid over 2 min, then to 18% acetonitrile with 0.1% formic acid over 18 min, followed by 100% acetonitrile and water washing for 6 min each.

Figure 4A:
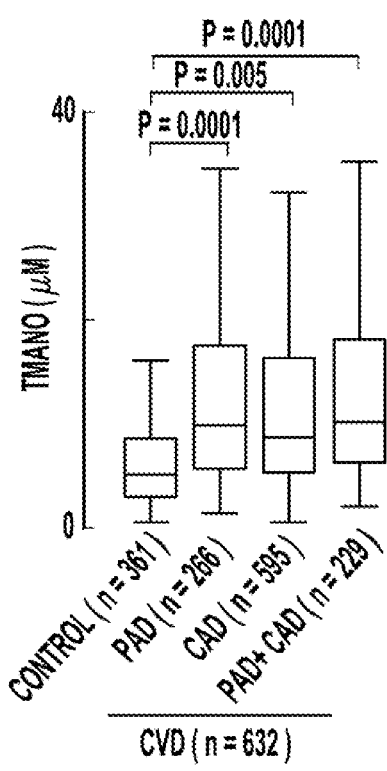
FIGS. 4A-C provide the results of a case/control study examining the relationship between plasma concentrations of TMANO and the prevalence of atherosclerotic CVD. Plasma was isolated from sequential subjects undergoing diagnostic cardiac catheterization with CVD (n=632) and from control subjects (n=361).
Figure 4B:
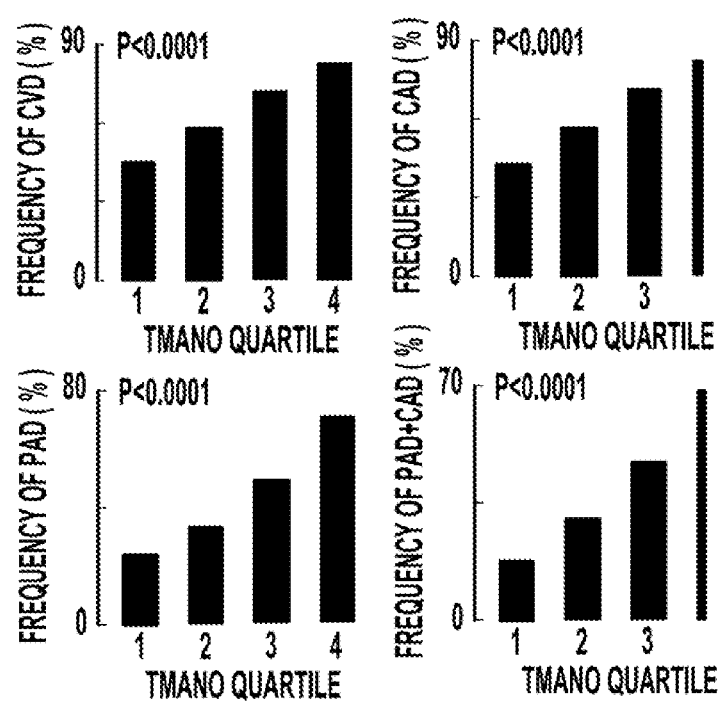

Shown in FIG. 4 and Tables 2a and 2b are results of the first independent clinical validation study to show TMANO predicts risk of having CVD, CAD, PAD or the combination of CAD and PAD amongst approximately 500 sequential men and 500 sequential women undergoing diagnostic cardiac catheterization. Table 2a shows the patient characteristics and demographics of the subjects with CVD versus those without clinical or angiographic evidence of cardiovascular disease. FIG. 4a is a box whisker plot of the levels of TMANO amongst those with CVD versus those without CVD in the study cohort. FIG. 4b shows frequency plots of TMANO levels stratified by quartile of the entire population versus the likelihood of having CVD, CAD, PAD or CAD+

Figure 4C:
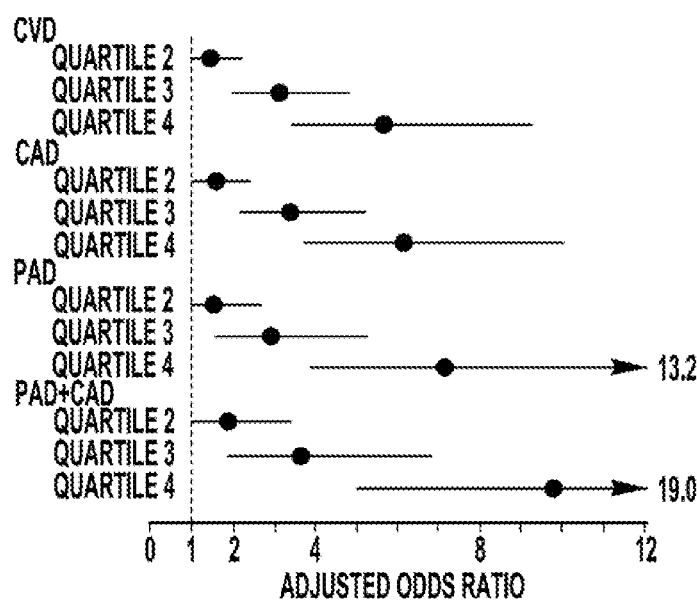

PAD for the population. Note that increasing levels of TMANO strongly associate with increased chance of having CVD, CAD, PAD or CAD+PAD. FIG. 4c and Table 2b show the odds ratio and 95% confidence intervals for TMANO levels versus having CVD, CAD, PAD or CAD+PAD following adjustments for traditional cardiac risk factors. These results show measurement of TMANO levels in a large clinical study identify individuals who have risk for having CVD, CAD, PAD or CAD+PAD.

TABLE 2a

Demographics of CVD prevalence

| Characteristic | Controls (n = 361) | Patients with CVD (n = 632) | P value |
|---|---|---|---|
| Age, mean (SD), y | 61.1 (7.8) | 65.4 (9.8) | <0.001 |
| Women, % | 52.4 | 52.1 | 0.98 |
| Diabetes, % | 14.0 | 41.3 | <0.001 |
| Hypertension, % | 28.2 | 17.5 | 0.25 |
| History of smoking, % | 52.4 | 56.0 | 0.73 |
| Current smoking, % | 4.8 | 5.7 | 0.80 |
| LDL cholesterol, median (IQR), mg/dL | 108 (85-130) | 95 (77-122) | <0.001 |
| HDL cholesterol, median (IQR), mg/dL | 49 (40-63) | 42 (35-53) | <0.001 |
| Triglycerides, median (IQR), mg/dL | 115 (82-165) | 139 (103-201) | <0.001 |
| CRP, median (IQR), mg/dL | 1.6 (0.8-3.9) | 3.1 (1.1-7.7) | <0.001 |
| Framingham Risk Score, mean (SD) | 13.3 (3.1) | 14.6 (3.6) | <0.001 |
| MDRD (GFR), mean (SD) | 87.6 (27.2) | 81.9 (50.7) | 0.05 |
| Medication | | | |
| ACEI, % | 33.0 | 54.6 | <0.001 |
| Statin, % | 28.0 | 63.4 | <0.001 |
| Aspirin, % | 54.6 | 75.0 | <0.001 |

TABLE 2b

Odds ratio (95% CI) of cardiovascular disease (CVD) risk according to quartiles of TMANO Quartile TMANO

| | Quartile | | | |
|---|---|---|---|---|
| TMANO (μM) | 1 (≤4.1) | 2 (4.1-7.0) | 3 (7.0-12.4) | 4 (≥12.4) |
| PAD, Cases (n = 266), Controls (n = 361) | | | | |
| Unadjusted | 1.0 | 157 (0.98-2.54) | 3.01 (1.87-4.87) | 7.39 (4.53-12.06) |
| Model α | 1.0 | 1.56 (0.91-2.67) | 2.94 (1.64-5.26) | 7.18 (3.90-13.22) |
| CAD, Cases (n = 595), Controls (n = 361) | | | | |
| Unadjusted | 1.0 | 1.70 (1.19-2.45) | 3.23 (2.21-4.71) | 5.62 (3.72-8.49) |
| Model α | 1.0 | 1.62 (1.09-2.42) | 3.42 (2.22-5.27) | 6.16 (3.76-10.09) |
| PAD + CAD, Cases (n = 229), Controls (n = 361) | | | | |
| Unadjusted | 1.0 | 1.97 (1.16-3.35) | 4.04 (2.39-6.83) | 9.48 (5.56-16.18) |
| Model α | 1.0 | 1.87 (1.03-3.38) | 3.62 (1.92-6.81) | 9.77 (5.02-19.00) |
| CVD, Cases (n = 632), Controls (n = 361) | | | | |
| Unadjusted | 1.0 | 1.59 (1.11-2.26) | 2.94 (2.03-4.26) | 5.29 (3.52-7.93) |
| Model α | 1.0 | 1.53 (1.04-2.27) | 3.18 (2.08-4.87) | 5.72 (3.51-9.31) |

Figure 5A:
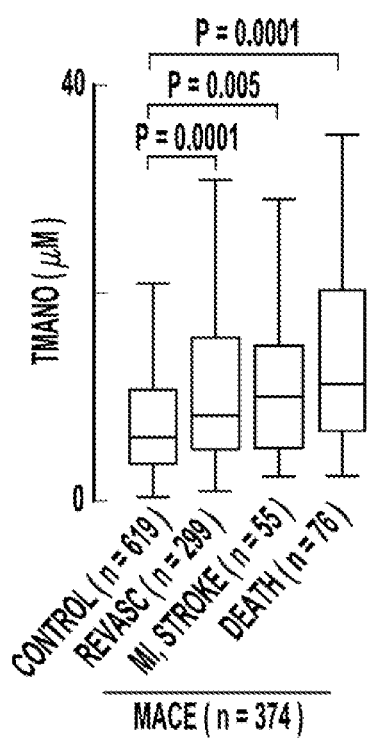
Figure 5B:
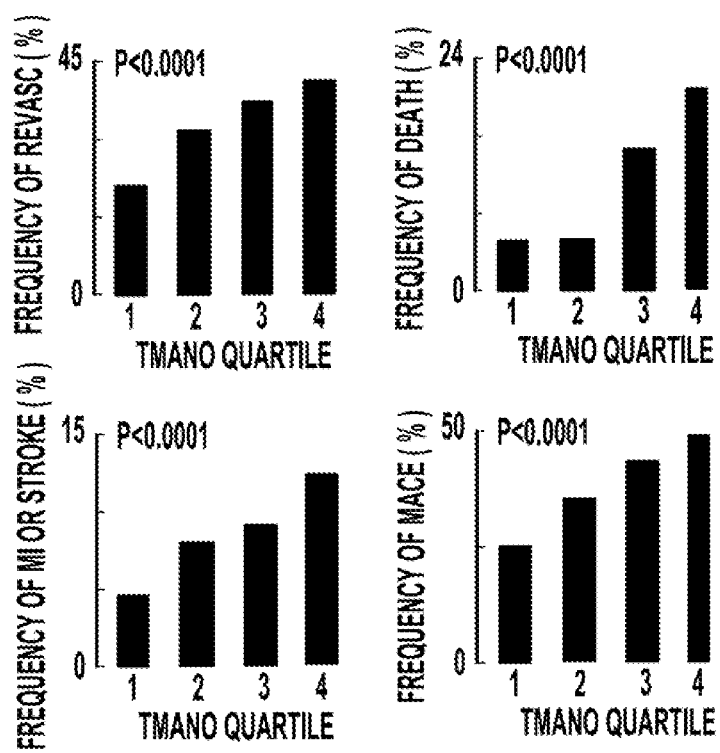

Shown in FIG. 5 and Tables 3a and 3b are the results of a second clinical validation study showing that TMANO levels predict incident 3 year risks of experiencing a nonfatal MI or stroke, a revascularization event, death, or the composite (MACE, major adverse cardiac event) amongst approximately 500 sequential men and 500 sequential women undergoing diagnostic cardiac catheterization. Table 3a shows the patient characteristics and demographics of the subjects stratified by those who experience a MACE over the ensuing 3 year period following enrollment versus those without MACE. FIG. 5a is a box whisker plot of the levels of TMANO amongst those who experience future MACE versus those who don't in the study cohort. FIG. 5b shows frequency plots of TMANO levels stratified by quartile of the entire population versus the likelihood of experiencing an incident non-fatal MI or stroke, revascularization event (CABG, angioplasty or stent), death, or the composite (MACE) for the entire population. Note that increasing levels of TMANO strongly predict incident 3 year risk for non-fatal MI or stroke, revascularization event (CABG, angioplasty or stent), death, or the composite (MACE). FIG. 5c and Table 3b show the odds ratio and 95% confidence intervals for TMANO levels versus the incident 3 year risk for non-fatal MI or stroke, revascularization event (CABG, angioplasty or stent), death, or the composite (MACE) following adjustments for traditional cardiac risk factors. These results show measurement of TMANO levels serves as a strong and independent predictor of incident 3 year risk for non-fatal MI or stroke, revascularization event (CABG, angioplasty or stent), death, or the composite (MACE).

TABLE 3a

Demographics of subjects with future risk of MACE (Revasculation, MI, stroke, or death).

| Characteristic | Patients without MACE (n = 619) | Patients with MACE (n = 374) | P value |
|---|---|---|---|
| Age, mean (SD), y | 62.8 (8.9) | 65.7 (9.7) | <0.001 |
| Women, % | 50.6 | 34.0 | 0.50 |
| Diabetes, % | 23.4 | 44.9 | <0.001 |
| Hypertension, % | 68.5 | 84.5 | <0.001 |
| History of smoking, % | 54.9 | 54.8 | 0.98 |
| Current smoking, % | 5.8 | 4.5 | 0.53 |
| LDL cholesterol, median (IQR), mg/dL | 103 (82-128) | 94 (76-122) | 0.003 |
| HDL cholesterol, median (IQR), mg/dL | 47 (37-58) | 41 (34-52) | <0.001 |
| Triglycerides, median (IQR), mg/dL | 127 (92-185) | 140 (103-201) | <0.001 |
| CRP, median (IQR), mg/dL | 2.7 (1.3-6.1) | 3.1 (1.4-6.8) | 0.14 |
| Framingham Risk Score, mean (SD) | 13.7 (3.4) | 14.8 (3.5) | <0.001 |
| MDRD (GFR), mean (SD) | 88.3 (47.8) | 79.1 (35.8) | 0.0002 |
| Medication | | | |
| ACEI, % | 40.5 | 57.0 | 0.001 |
| Statin, % | 43.1 | 65.8 | <0.001 |
| Aspirin, % | 61.9 | 77.0 | <0.001 |

TABLE 3b

Odds ratio (95% CI) of incident risk for MACE (revasculation (Revasc), non-fatal MI, stroke or death) according to quartiles of TMANO Quartile TMANO

| TMANO (µM) | Quartile | | | |
|---|---|---|---|---|
| | 1 (≤4.1) | 2 (4.1-7.0) | 3 (7.0-12.4) | 4 (≥12.4) |
| Revasc, Cases (299), Controls (n = 619) | | | | |
| Unadjusted | 1.0 | 1.74 (1.15-2.64) | 2.21 (1.47-3.34) | 2.61 (1.73-3.94) |
| Model ζ | 1.0 | 1.49 (0.96-2.31) | 1.89 (1.21-2.96) | 2.57 (1.64-4.02) |
| Non-fatal MI or stroke, Cases (55), Controls (n = 619) | | | | |
| Unadjusted | 1.0 | 1.81 (0.76-4.29) | 2.05 (0.86-4.87) | 2.90 (1.26-6.66) |
| Model ζ | 1.0 | 1.43 (0.55-3.72) | 1.59 (0.62-4.10) | 2.93 (1.16-7.42) |
| Death, Cases (76), Controls (n = 619) | | | | |
| Unadjusted | 1.0 | 1.05 (0.42-2.64) | 3.16 (1.46-6.82) | 4.78 (2.28-10.05) |
| Model ζ | 1.0 | 0.72 (0.26-2.04) | 2.55 (1.10-5.90) | 3.93 (1.71-9.03) |
| MACE, (Revasc, MI, stroke, or death), Cases (n = 374), Controls (n = 619) | | | | |
| Unadjusted | 1.0 | 1.63 (1.11-2.40) | 2.25 (1.54-3.30) | 2.78 (1.90-4.07) |
| Model ζ | 1.0 | 1.37 (0.91-2.08) | 1.86 (1.22-2.83) | 2.62 (1.72-3.99) |

ζ Model consisted of Framigham risk score, MDRD, CRP and TMANO

To obtain the data shown in FIG. 5, plasma was analyzed for TMANO content from case subjects (n=374) who underwent diagnostic cardiac catheterization and experienced MACE in the 3-year period after study enrollment. Parallel analyses were also performed on plasma from control subjects (n=619) who underwent diagnostic cardiac catheterization and did not experience MACE over the 3 years after study enrollment.

Example 2

Using a sequential case: control design, metabolomics analyses (i.e., systematic study of the unique chemical fingerprints left behind by specific cellular processes) were performed by LC/MS to identify small molecules in plasma that identify subjects at risk for MACE over the ensuing 3 year period. Only 13 analytes met the acceptability criterion for discriminating risk in both learning and validation cohorts. Of these metabolites, regression analysis revealed three analytes (with mass-to-charge ratios (m/z) of 76, 104 and 118) were strongly correlated (P<0.0001), suggesting their connection via a common pathway. Using LC/MS/MS, chemical derivatization, GC/MS and feeding of mice with various choline isotopomers, the species with m/z=76, 104 and 118 were unambiguously identified as trimethylamine N-oxide (TMANO), choline and betaine, respectively. Prognostic utility of plasma TMANO, choline and betaine levels for prediction of 3 year MACE risk was confirmed in 1,020 sequential consenting subjects undergoing diagnostic left heart catheterization. Compared to the lowest quartile, subjects with high (4.sup.th quartile) levels of either TMANO, choline or betaine were >3-fold more likely to have CAD, >5.0-fold more likely to have PAD, and >2-fold more likely to experience a MACE over the ensuing 3 years independent of Framingham risk factors and CRP.

Although only a few exemplary embodiments have been described in detail, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure.

We claim:

1. A method of detecting trimethylamine-n-oxide (TMANO) in a sample comprising:
   a) obtaining a sample, wherein said sample is from a non-TMANO treated human subject who is known to be at risk for cardiovascular disease (CVD) or is known to have CVD, wherein said sample is a urine sample, serum sample, or plasma sample;
   b) introducing at least a portion of said sample into an analytical device under conditions such that the concentration of TMANO present in said sample is determined, wherein said analytical device comprises: i) an NMR spectrometer, a UV/Vis spectrometer, or a mass spectrometer, and ii) equipment to provide physical separation of said TMANO prior to determining said concentration; and
   c) graphically displaying said subject's risk of having cardiovascular disease as higher than normal based on determining said level of TMANO in said sample being higher than a control value derived from a human general population or a group of humans without symptoms of cardiovascular disease.

2. The method of claim 1, wherein the analytic device comprises a mass spectrometer.

3. The method of claim 1, wherein the analytic device comprises an NMR spectrometer.

4. The method of claim 1, wherein the analytic device comprises a UV/Vis spectrometer.

5. The method of claim 1, wherein said control value is derived from a group without symptoms of cardiovascular disease.

6. The method of claim 1, wherein said subject has chest pain.

7. The method of claim 1, wherein said sample is a urine sample.

8. The method of claim 1, wherein said sample is a plasma sample.

9. The method of claim 1, wherein said sample is a serum sample.

10. The method of claim 1, wherein said sample is obtained from said subject after the administration of a CVD therapeutic.

\* \* \* \* \*